US009962519B2

(12) United States Patent
Charest et al.

(10) Patent No.: US 9,962,519 B2
(45) Date of Patent: May 8, 2018

(54) SEEPING FLOW ANTI-CLOTTING BLOOD CATHETER

(71) Applicant: The Charles Stark Draper Laboratory, Inc., Cambridge, MA (US)

(72) Inventors: Joseph L. Charest, Cambridge, MA (US); James Hsiao, Watertown, MA (US); Christopher DiBiasio, Stoughton, MA (US); Kevin A. Hufford, St. Petersburg, FL (US)

(73) Assignee: THE CHARLES STARK DRAPER LABORATORY, INC., Cambridge, MA (US)

( * ) Notice: Subject to any disclaimer, the term of this patent is extended or adjusted under 35 U.S.C. 154(b) by 8 days.

(21) Appl. No.: 14/595,938

(22) Filed: Jan. 13, 2015

(65) Prior Publication Data
US 2017/0100564 A1 Apr. 13, 2017

Related U.S. Application Data

(60) Provisional application No. 61/927,325, filed on Jan. 14, 2014.

(51) Int. Cl.
*A61M 25/14* (2006.01)
*A61M 25/00* (2006.01)

(52) U.S. Cl.
CPC .... *A61M 25/0029* (2013.01); *A61M 25/0043* (2013.01); *A61M 2205/3334* (2013.01)

(58) Field of Classification Search
CPC ............ A61M 25/007; A61M 25/0043; A61M 25/0045; A61M 2205/3334; A61M 2025/0057; A61M 25/0029

USPC ........................................................ 604/266
See application file for complete search history.

(56) References Cited

U.S. PATENT DOCUMENTS

| 5,776,184 A | 7/1998 | Tuch |
| 7,175,734 B2 * | 2/2007 | Stewart ............. A61B 18/1492 |
| | | 156/290 |
| 2004/0064129 A1 * | 4/2004 | Deniega ............ A61M 25/0043 |
| | | 604/523 |

(Continued)

FOREIGN PATENT DOCUMENTS

| EP | 0 667 131 B1 | 8/1995 |
| WO | WO-90/06150 A1 | 6/1990 |

(Continued)

OTHER PUBLICATIONS

International Search Report and Written Opinion dated Apr. 15, 2015 in PCT Application No. PCT/US2015/011223.

*Primary Examiner* — Nathan R Price
*Assistant Examiner* — John Doubrava
(74) *Attorney, Agent, or Firm* — Lando & Anastasi, LLP

(57) ABSTRACT

The device and methods described herein relate to a seeping flow catheter. The seeping flow catheter includes a porous material. The inner face of the porous material defines the lumen of the catheter. The porous material is configured such that fluid can flow along the length of the catheter, between the inner face and outer face of the porous material. As the fluid flows through the porous material, the fluid can seep into the lumen of the catheter through the inner face or out of the catheter through the outer face of the porous material. Portions of the inner or outer face can include a lining that substantial reduces the perfusion of the fluid through the lined areas.

14 Claims, 8 Drawing Sheets

(56) References Cited

U.S. PATENT DOCUMENTS

| | | | |
|---|---|---|---|
| 2006/0229573 A1 | 10/2006 | Lamborne | |
| 2009/0326508 A1 | 12/2009 | Braun et al. | |
| 2012/0310085 A1* | 12/2012 | Herweck | A61M 25/0023 600/434 |
| 2014/0031741 A1* | 1/2014 | Stice | A61M 25/0009 604/28 |

FOREIGN PATENT DOCUMENTS

| | | |
|---|---|---|
| WO | WO-2004/033013 A1 | 4/2004 |
| WO | WO-2007/027545 | 3/2007 |

* cited by examiner

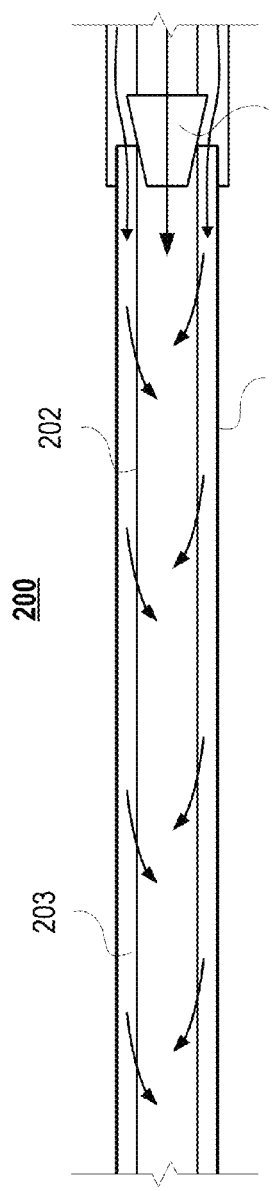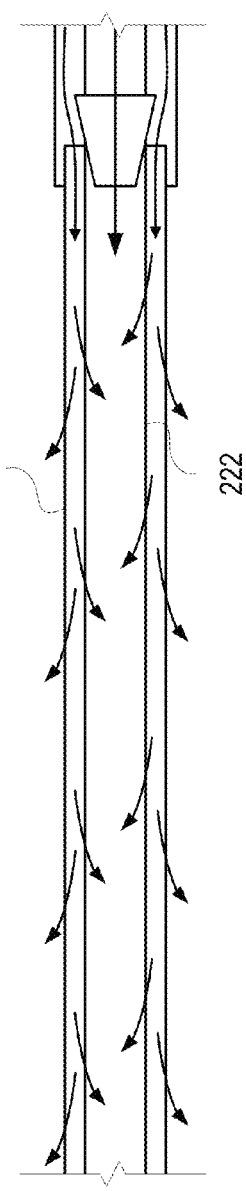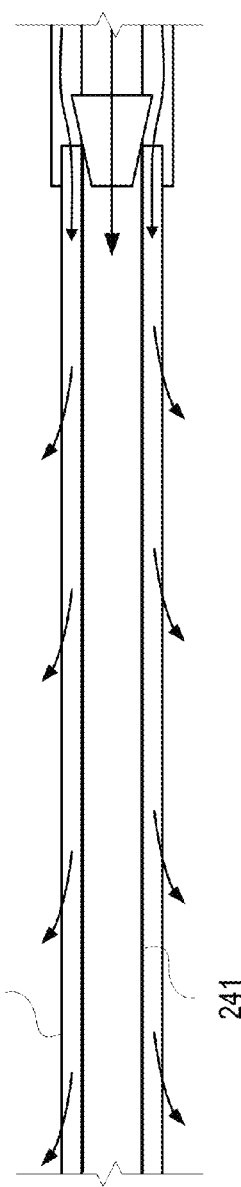

SEEPING FLOW ANTI-CLOTTING BLOOD CATHETER

CROSS-REFERENCE TO RELATED APPLICATIONS

This application claims priority to U.S. Provisional Patent Application No. 61/927,325 filed on Jan. 14, 2014 and titled "SEEPING FLOW ANTI-CLOTTING BLOOD CATHETER," which is herein incorporated by reference in its entirety.

BACKGROUND OF THE DISCLOSURE

Catheters are tube-like medical devices that provide access to a patient. Catheters may be used to inject or remove agents, medications, or body fluids from a patient. Catheters can fail from extended periods of use. The decreased performance of a catheter can be the result of material clogging the catheter. The clogs may be the result of debris or from the formation of clots or biofilms within the lumen of the catheter.

SUMMARY OF THE DISCLOSURE

According to one aspect of the disclosure, a catheter includes an elongated tube having a distal end and a proximal end. The elongated tube includes a porous material with an interior face and an exterior face. The interior face defines a lumen along a central axis of the elongated tube. The porous material is configured such that a fluid can flow between the interior face and the exterior face of the porous material and seep out of the porous material through the exterior face and/or the interior face. The catheter also includes a first lining that covers at least a portion of the exterior face. The lining substantially limits perfusion through the exterior face at the portion covered by the first linings.

In some implementations, the catheter also includes a fitting coupled to the proximal end of the elongated tube. The fitting is configured to flow a first fluid into the porous material and a second fluid into the lumen of the catheter. In some implementations, the first fluid is different than the second fluid.

In certain implementations, the resistance to flow through the inner face or exterior face of the porous material is between about 10 and about 100 times higher than the resistance to flow through the porous material along an axis parallel to the central axis of the elongated tube. In some implementations, the catheter includes a second lining that covers at least a portion of the interior face. In some implementations, the second lining covers substantially all of the interior face except a portion toward the distal end of the elongated tube. The first lining may cover substantially all of the exterior face except a portion toward the distal end of the elongated tube.

In some implementations, the thickness of the porous material is between about 20 μm and about 1 mm and the porous material includes phase inversion polyethersulfone.

In some implementations, the interior face has a first porosity at a first distance from the proximal end of the elongated tube and a second porosity at a second distance from the proximal end of the elongated tube.

According to another aspect of the disclosure, a method includes providing a catheter for flowing a fluid. The catheter includes a porous material having an interior face and an exterior face. The interior face of the catheter defines a central lumen of the catheter. The method also includes flowing a first fluid through the porous material of the catheter and flowing a second fluid through the central lumen of the catheter. In the method, the first fluid seeps into the central lumen of the catheter through the interior face of the porous material.

In some implementations, the method also includes flowing an anti-coagulant through the porous material of the catheter. The first fluid can be flowed through the porous material at a pressure configured to force the first fluid to seep through the interior face of the catheter and into the central lumen of the catheter. In some implementations, the method includes flowing the fluids through the catheter at a pulsatile flow rate.

In some implementations, the method includes flowing a first agent through the central lumen of the catheter. In certain implementations, a second agent, which counteracts the first agent, is flowed through the porous material of the catheter.

In some implementations, the porous interior face has a first porosity at a first distance from an inlet of the catheter and a second porosity at a second distance from the inlet of the catheter. In some implementations, the method includes seeping the first fluid out of the catheter through the external face of the porous material.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which:

FIGS. 2A-2E illustrate cross-sectional views of example seeping flow catheters with different lining configurations.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

Figure 1:
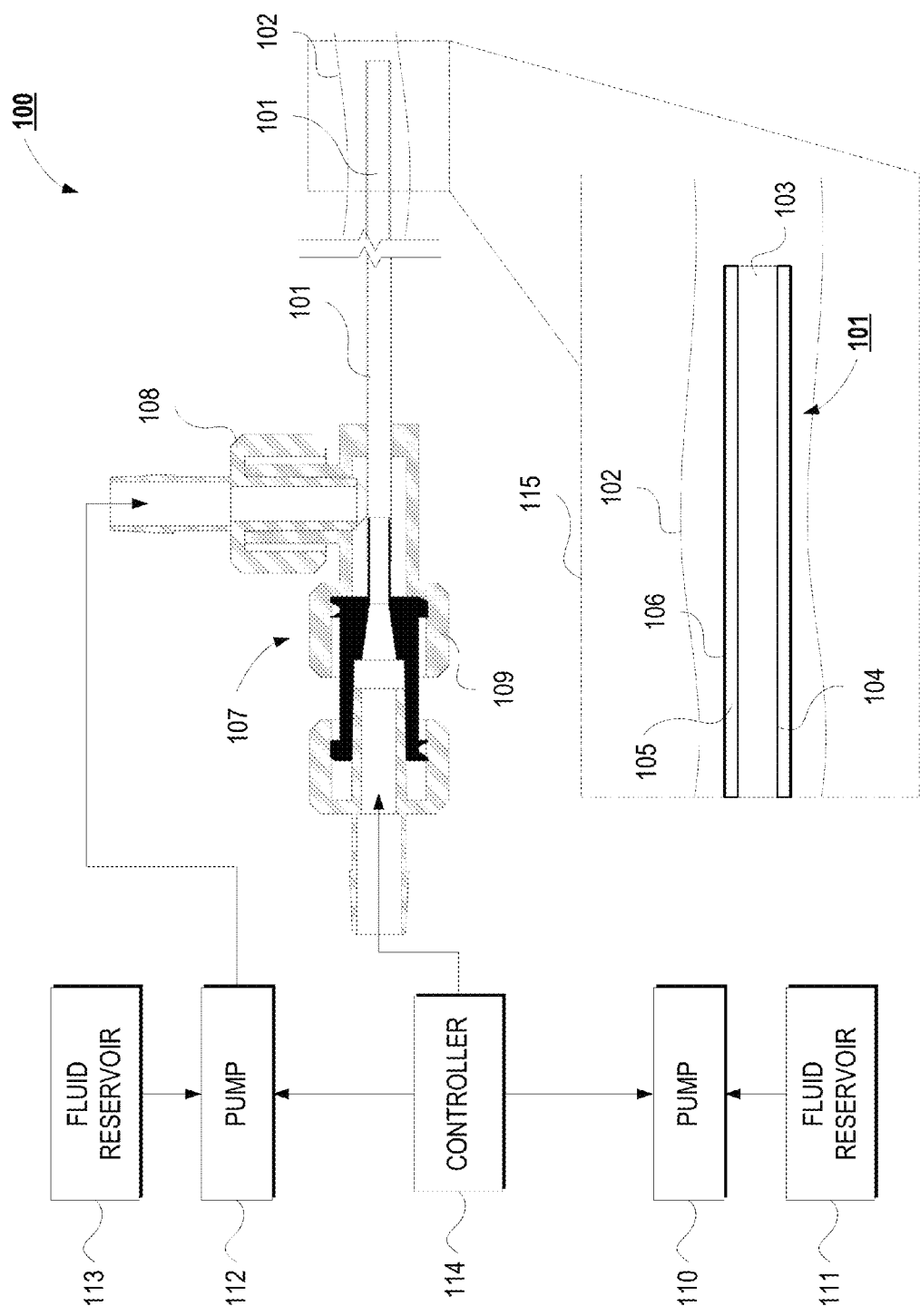
FIG. 1 illustrates a schematic of system using an example seeping flow catheter.

FIG. 1 is a schematic of a system 100 using a seeping flow catheter 101. FIG. 1 provides a cross-sectional view of the catheter 101 and nozzle 107. The catheter 101 is inserted into an internal lumen 102 of a patient. The internal lumen 102 can be any vessel, duct, or body cavity of the patient's body. Box 115 provides an enlarged view of a portion of the catheter 101 inserted into the internal lumen 102 of the patient. The catheter 101 includes a porous material 105. The porous material 105 has an inner face 104 and the exterior face 106. The catheter's lumen 103 is defined by the inner face 104 of the catheter 101. A nozzle 107 injects fluid into the porous material 105 via a secondary fitting 108 and into the lumen 103 via a primary fitting 109. A pump 110 flows fluid from the fluid reservoir 111 to the primary fitting 109, and a second pump 112 flows fluid from the fluid reservoir 113 to the secondary fitting 108. The pumps 110 and 112 are controlled by the controller 114.

The catheter 101 is described in greater detail in relation to FIGS. 2A-5. Example methods of manufacture and uses of a seeping catheter are described in relation to FIG. 7.

As an overview, the catheter 101 is a "seeping" catheter. The term seeping relates to a fluid seeping through the inner face 104 of the porous material 105 into the catheter's lumen 103 and/or out of the catheter 101 through the exterior face 106 of the porous material 105 as fluid flows through the porous material 105 of the catheter 101. As described below, fluid seeping into the catheter's lumen 103 creates a barrier that reduces the interaction that a primary fluid (e.g., blood) flowing through the catheter's lumen 103 has with the inner face 104. In some implementations, the barrier reduces the resistance to flow of the primary fluid through the lumen 103 by altering the boundary conditions and effectively increasing the internal diameter of the lumen 103. In some implementations, the fluid seeping out of the exterior face 106 reduces catheter 101 encapsulation. Encapsulation may occur when a catheter is in-dwelling for long periods of time in the patient's body and the patient's body begins to bond to, encapsulate, adhere clots or clotting agents to, adhere cells to, or endothelialize the catheter. Reducing encapsulation of the catheter 101 makes the catheter 101 easier to remove from a patient and increases patency duration. In some implementations, encapsulation or thrombosis is reduced by seeping an agent out of the catheter 101. The agent can inhibit endothelialization or the buildup of other material within or on the catheter 101. In other implementations, the seeping flow washes away cell buildup on the exterior of the catheter 101. The seeping flow can be a continuous flow or a pulsed flow that is periodically passed through the catheter 101. In some implementations, the catheter 101 is impregnated with an agent that passively prevents buildup of material on the inner face 104 or the exterior face 106. In some implementations, the agent impregnated into the catheter 101 can include an inhibitor of clotting such as heparin or citrate; a hydrophobic or hydrophilic surface modifier, a substance to change the charge of the inner face 104, exterior face 106, or catheter 101; a thrombolytic agent configured to dissolve buildup; or a protease configured to dissolve proteins In some implementations, the porous material 105 is between about 20 μm and about 2 mm, between about 20 μm and about 1 mm, or between about 20 μm and about 50 μm thick. In some implementations, the catheter 101 is the same length of a standard medical catheter. In other implementations, the catheter 101 is coupled to a standard medical catheter and the catheter 101 portion of the catheter is between about 5 cm and about 30 cm, between about 10 cm and 20 cm, or between about 5 cm and 15 cm long. In some implementations, the catheter 101 is manufactured in the French catheter scale of between 1 gauge and 34 gauge.

The system 100 also includes a nozzle 107 that injects fluid into the catheter's lumen 103 and the porous material 105. The nozzle 107 includes a primary fitting 109 to flow fluid into the catheter's lumen 103, and a secondary fitting 108 to flow fluid into the catheter's porous material 105. In some implementations, the nozzle 107 is based on the port or Luer fittings commonly found in medical catheters and other medical fluid flow devices. In some implementations, the primary fitting 109 and the secondary fitting 108 are located at separate lengths along the catheter 101. For example, the secondary fitting 108 can be a collar that wraps around the circumference of the catheter 101 at a specific location along the length of the catheter 101. The collar can inject fluid into the porous material 105 through the exterior face 106. In some implementations, the secondary fitting 108 and the primary fitting 109 flow fluid into their respective parts of the catheter 101 from a single fluid source. In other implementations, as illustrated in FIG. 1, the secondary fitting 108 and the primary fitting 109 flow fluid into the respective parts of the catheter 101 from different fluid sources.

The system 100 includes the first pump 110 and the second pump 112, which are connected to the first fluid reservoir 111 and the second fluid reservoir 113, respectively. As described above, in some implementations, a single pump and fluid reservoir is used to deliver fluid to the catheter's lumen 103 and the porous material 105. The pump 112 and the pump 110 are controlled by the controller 114. The controller 114 controls the rate, duration, and waveform of the fluid flow generated by the pumps 110 and 112. For example, the controller 114 can cause the pumps 112 and 110 to flow fluid through the catheter 101 at a substantially constant flow rate or in a pulsatile manner. In some implementations, the controller 114 is also configured to control the pressure of fluids flowing within the porous material 105 and the lumen 103. For example, a first fluid flowing through the porous material 105 can be pressurized to a level higher than a second fluid flowing through the lumen 103 such the first fluid seeps into the lumen 103 and the second fluid does not seep into the porous material 105. In some implementations, the flow rate of the fluid through the porous material 105 is titrated such that the seeping flow into the lumen 103 of the catheter 101 is between about 0.1% and about 5%, between about 5% and about 30%, between about 10% and about 30%, or between about 20% and about 30% of the flow rate of the fluid into the lumen 103 through the primary fitting 109. In some implementations, a bolus or series of pulses of the fluid flow is flowed through the porous material 105 to "debulk" the pores of the exterior face 106 and inner face 104. For example, as blood flows through the lumen 103 of the catheter 101, the pores of the inner face 104 can become clogged. The pulsatile flow can clear the pores of material such that fluid can continue to seep into the lumen 103 of the catheter 101. In some implementations, the fluid seeps out of the porous material 105 after the fluid pressure in the porous material 105 has reached a predetermined threshold. In some implementations, the controller 114 is configured to cause the pump 112 to maintain a fluidic pressure in the porous material 105 above the predetermined threshold.

In some implementations, the pumps 110 and 112 are infusion pumps, perfusion pumps, peristaltic pumps, or similar pumps used in combination with medical grade catheters. In some implementations, the pump 110 is used to create a vacuum such that the catheter 101 is used for fluid extraction from the patient. For example, the catheter 101 may be used for post-operative drainage. In this example, the pump 112 can still inject a fluid into the porous material 105 such that the fluid seeps out of the porous material 105 to assist in the flow of the evacuated fluid through the catheter 101 or to reduce encapsulation of the catheter 101.

FIGS. 2A-2E illustrate cross-sectional views of example seeping catheters with different lining configurations. As described above, the body of the catheter 101 is defined by a porous material 105. As a fluid flows through the porous material 105, the fluid can seep out of the catheter 101 through the exterior face 106 and inner face 104. In some implementations, a lining is applied to the exterior face 106 and/or inner face 104 to reduce the permeability of the fluid through the face to which the lining is applied.

FIG. 2A illustrates a cross-sectional view of an example seeping catheter 200. The catheter 200 includes a lining 201 on the outer face of the catheter 200. As illustrated no lining is applied to the inner face 202 of the catheter 200. The lining 201 can include a coating, such as but not limited to adhesives or chemical vapor deposition coatings that when dried substantially limits perfusion through the areas to which it is applied. In some implementations, heat or chemical solvents may be applied to the face to create the lining. Heat or solvents create the lining by melting the surface of the porous material, which seals the pores. In some implementations, the lining substantially prohibits perfusion through the face to which it is applied. In other implementations, the lining reduces the perfusion through the face to which it is applied when compared to the face without the application of the lining and in other implementations, the lining is configured to allow a predetermined level of perfusion through the applied face. For example, the lining may be configured to allow the perfusion of molecules below a specific molecular weight. In other implementations, the lining is selectively applied to specific areas to limit perfusion to various levels in those areas. In some implementations, the effect of the catheter 200 is created by using the porous material 203 as a lining for the lumen of a standard catheter or, as in the below described catheter 240, a lining for the external face of a standard catheter. In some implementations, the lining is coated with one or more of an anticoagulant, antibiotic, or antithrombotic.

As fluid flows through the porous material 203 of the catheter 200, the lining 201 substantially prevents the fluid from exiting the catheter 200 through the outer face. Rather, the fluid seeps into the internal lumen of the catheter 200 through the inner face of the catheter 200. In some implementations, the fluid seeping into the internal lumen of the catheter limits the interaction a primary fluid injected into the lumen via the primary fitting 204 has with the inner face 202. Limiting the interaction of the primary fluid and the inner face 202 changes the effective boundary conditions of the primary fluid's flow through the inner lumen of the catheter 200. The change in effective boundary conditions reduces the resistance to flow and increases the effective diameter of the inner lumen. In some implementations, reducing the resistance to flow reduces pump losses when flowing fluids through the catheter. When blood is flowed through the catheter, the reduced resistance can also reduce the potential of clotting or thrombus formation in the catheter.

In some implementations, the example catheter 200 is used to deliver agents to the primary fluid flowing through the lumen of the catheter 200. The agents can include blood thinners, anti-coagulants, coagulants, medications, thrombolytics, antibiotics, antivirals, a dyes, labels, or tracing substances to allow visualization of the catheter or fluid flowing through it, a biological agents such as a proteins, peptides, DNA, RNA, RNAi, siRNA, or other nucleotide sequence, solutions to alter pH, solutions to alter compound concentrations in the blood, binding agents to chelate or bind entities in the blood, dissolved or other formats of gases such as oxygen, a capture agent to specifically tether/bind/capture an entity in the blood, an agent to alter the viscosity of a fluid in the lumen, toxin or an agent to counter a toxin, simple saline buffers or fluids, sugars, amino acids fats or other nutritive agents, inert molecules, volume expanders for the fluid in the lumen, any combination thereof, or agents to reverse (or counteract) one or more of the foregoing agents. For example, a first catheter configured similarly to catheter 200 (or other implementation described herein) may connect a patient to the input of a bypass machine and a second catheter configured similarly to catheter 200 (or other implementation described herein) may return the blood to the patient from the bypass machine. The first catheter can introduce heparin, a blood thinner, into the blood such that it does not clot in the bypass machine. Seeping protamine sulfate, a heparin reversal agent, into the blood as it returns to the patient via the second catheter reverses the effects of the heparin in the blood. The protamine sulfate can be introduced into the blood through the second catheter, such that reduced levels, and in some implementations substantially no, active heparin remains in the blood when it re-enters the patient's body. In another example, where the catheter 200 is used as part of a urinary catheter, antibiotics may be seeped into the lumen of the catheter to limit the formation of bacterial biofilms that can form in, and clog, urinary catheters and infect the patient.

FIG. 2B illustrates a cross-sectional view of an example seeping catheter 220. Neither the exterior face 221 or inner face 222 are covered with a lining. Thus, the fluid flowing through the porous material seeps through the exterior face 221 and the inner face 222. As in the catheter 200, the fluid seeping into the lumen through the inner face 222 can deliver an agent flowing through the lumen or be used to reduce the resistance to flow through the lumen. FIG. 2C describes the seeping of fluid through the outer face of a catheter and into the tissue surrounding the catheter.

FIG. 2C illustrates a cross-sectional view of an example seeping catheter 240. The inner face of the catheter 240 includes a lining 241 that substantially prevents fluid from seeping through the inner face of the catheter 240. The exterior face 242 is not coated with a lining to and thus fluid seeps out of the catheter 240 through the exterior face 242 when fluid is flowed through the porous material of the catheter 240. The extended placement of catheters can cause encapsulation of the catheter and/or the catheter can become a source of infection. In some implementations, the fluid seeping out of the exterior face 242 reduces encapsulation of the catheter 240. Encapsulation occurs when the patient's body begins to endothelialize or otherwise encapsulate a catheter. Encapsulation can make it difficult or painful to remove the catheter. The seeping of fluid through the exterior face 242 can limit the interaction of the tissue surrounding the catheter 240 and the catheter 240, reducing the occurrence of encapsulation. In some implementations, encapsulation is reduced by the flowing a fluid through the porous material of the catheter 240 that includes agents to prevent encapsulation. For example, agents that reduce vasculogenesis and angiogenesis can prevent endothelialization in an area local to the catheter 240. In some implementations, agents such as anti-inflammatories or antibiotics are seeped into the surrounding tissue through the catheter 240. For example, seeping an antibiotic into the tissue surrounding the catheter 240 to reduce the likelihood of an infection occurring due to long term placement of an indwelling catheter.

Figure 2D:
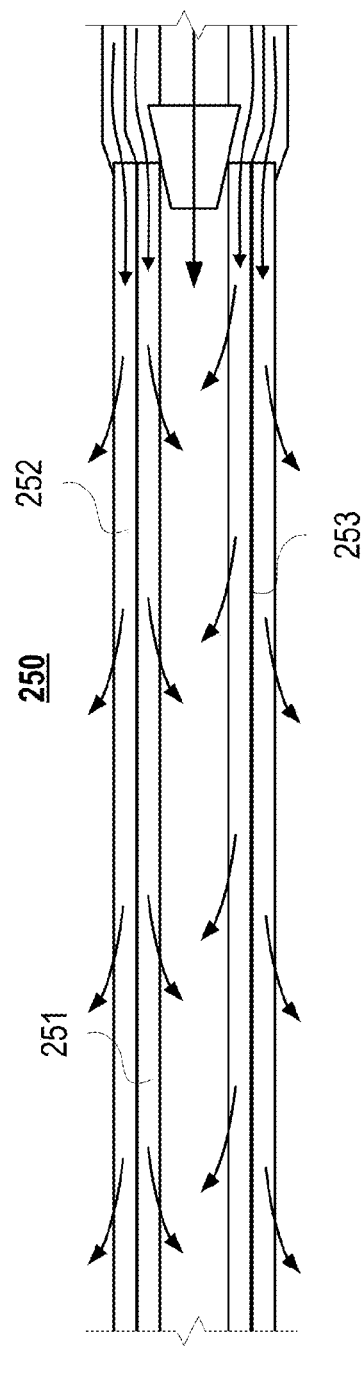

FIG. 2D illustrates a cross-sectional view of an example seeping catheter 250. The catheter 250 includes interior porous material 251 that seeps a fluid into the central lumen of the catheter and an exterior porous material 252 that seeps a fluid out of the catheter. The interior porous material 251 and exterior porous material 252 are separated by a lining 253. In some implementations, the fluid flowed through the interior porous material 251 and the exterior porous material 252 are different fluids and in other implementations the fluids are the same.

Figure 2E:
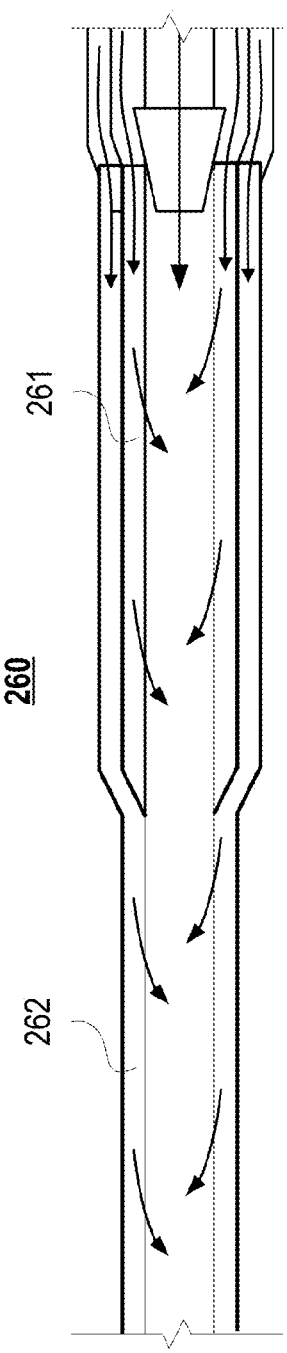

FIG. 2E illustrates a cross-sectional view of an example seeping catheter 260. The catheter 260 includes a plurality of porous materials. The first porous material 261 extends a first length along the catheter 260 and the second porous material 262 extends a second length along the catheter 260. In some implementations, the first porous material 261 is used to seep a first fluid into the catheter 260 along a first length of the catheter 260 and then a second fluid is seeped into the catheter 260 along a second length of the catheter through the second porous material 262. For example, a blood thinner may be seeped into the catheter 260 along a first length of the catheter 260 through the first porous material 261 and then an agent to counteract the blood-thinner may be seeped into the catheter 260 through the second porous material 262 before the blood enters a patient. In another implementation, the first porous material 261 is configured on the exterior of the second porous material 262 such that a first and second fluid can be seeped out of the catheter 260 at different lengths along the catheter 260.

Figure 3A:
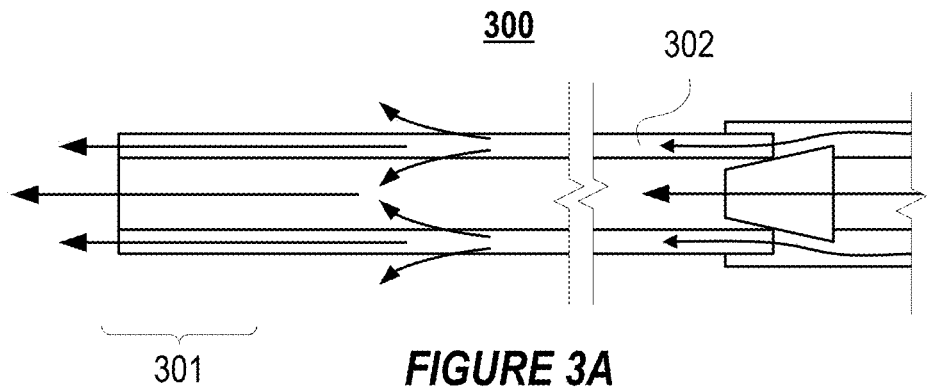
FIGS. 3A and 3B illustrate example tip configurations for a seeping flow catheter.
Figure 3B:
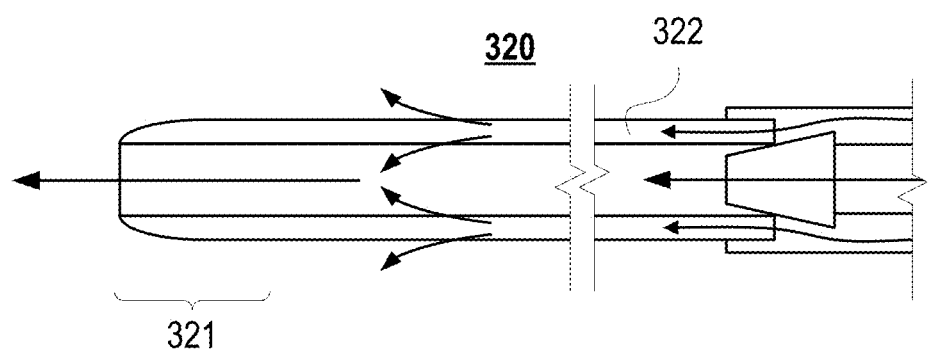

FIGS. 3A and 3B illustrate example tip configurations for a seeping catheter. FIG. 3A illustrates a seeping catheter with an open tip 301. The open tip 301 enables the fluid flowing through the porous material 302 to exit through the end of the catheter 300. For example, a saline solution may be flowed through the porous material 302 to debulk buildup that can occur near the tip of a catheter. In some implementations, both the interior and exterior face of the porous material 302 are covered with a lining such that a fluid exits the porous material 302 through substantially only the open tip of the catheter 300.

FIG. 3B illustrates a seeping catheter 320 with a closed tip 321. The closed tip 321 is sealed such that fluid does not exit through the end of the porous material 322. In some implementations, the closed tip 321 may be formed by applying a lining, such as the lining described above, to limit perfusion through the inner face and outer face of the catheter. In some implementations, a closed tip 321 design is used to create a pressure buildup of fluid within the porous material 322 such that the fluid in the porous material 322 can seep through inner or outer face of the catheter 320 upstream from the closed tip 321.

Figure 4:
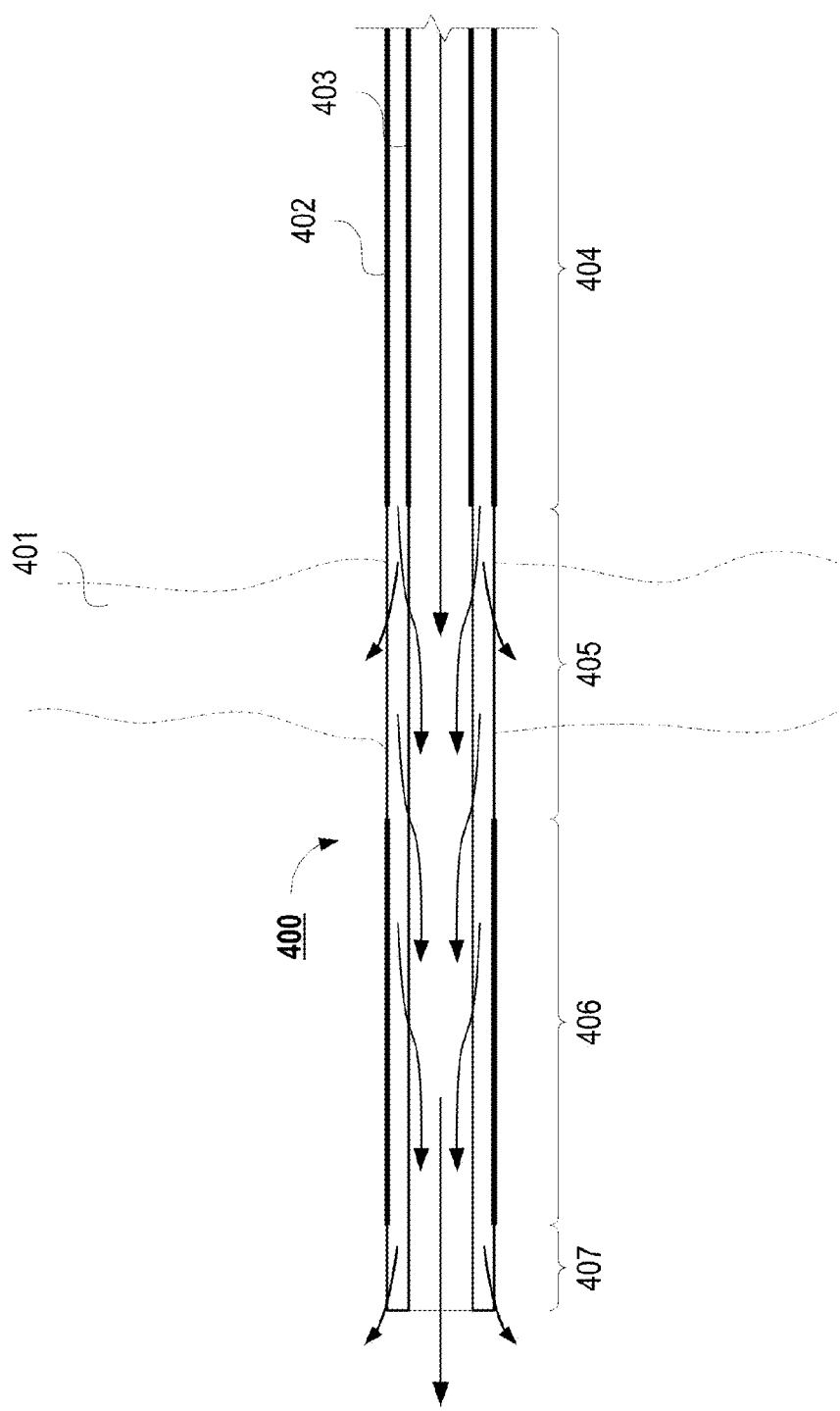
FIG. 4 illustrates a seeping flow catheter with a plurality of lining configurations.

FIG. 4 illustrates an example seeping catheter 400 with a plurality of lining configurations. The catheter 400 is implanted through tissue 401. For example, the seeping catheter 400 may be implanted into the abdominal cavity of a patient and the tissue 401 may be the abdominal wall of the patient. The seeping catheter 400 is configured to have a plurality of lining configurations on both the exterior face 402 and the inner face 403. In the section 404, both the exterior face 402 and the inner face 403 are lined to substantially prevent perfusion through the respective faces of the catheter 400. The section 404 represents the exterior portion of the seeping catheter 400. In some implementations, the lining configuration of the section 404 causes the seeping catheter 400 to behave like a standard catheter. For example, as with a standard catheter, substantially no fluid leaks into the lumen of the seeping catheter 400 or out through the exterior face 402 in the section 404 of the catheter 400.

In the section 405 of the seeping catheter 400, neither the exterior face 402 or the inner face 403 are lined, allowing fluid to perfuse through both the exterior face 402 and the inner face 403. In some implementations, as described above, fluid perfusing through the exterior face 402 may reduce the likelihood of the seeping catheter 400 becoming encapsulated by the tissue 401.

In the section 406 of the seeping catheter 400, the exterior face 402 is lined. As illustrated, fluid from the porous material of the seeping catheter 400 seeps into the internal lumen of the seeping catheter 400 but not through the exterior face 402 of the seeping catheter 400. As described above, the lining configuration of the section 406 can be used to introduce agents into the lumen of the catheter 400 and/or reduce the resistance to flow through the catheter 400.

At the tip 407, the exterior face 402 and the inner face 403 of the catheter 400 are not lined. In some implementations, a tip configuration with no lining enables the tip 407 of the catheter 400 to be debulked (i.e., material buildup near the tip 407 can be dislodged from the catheter 400). As illustrated in FIG. 4, the lining configurations change abruptly at the transition between sections. In some implementations, the lining configurations change gradually. For example, along a length of a catheter, a lining may gradually become thinner until it is substantially nonexistent. As the lining thins it allows a greater amount of perfusion through the face of the porous material.

Figure 5:
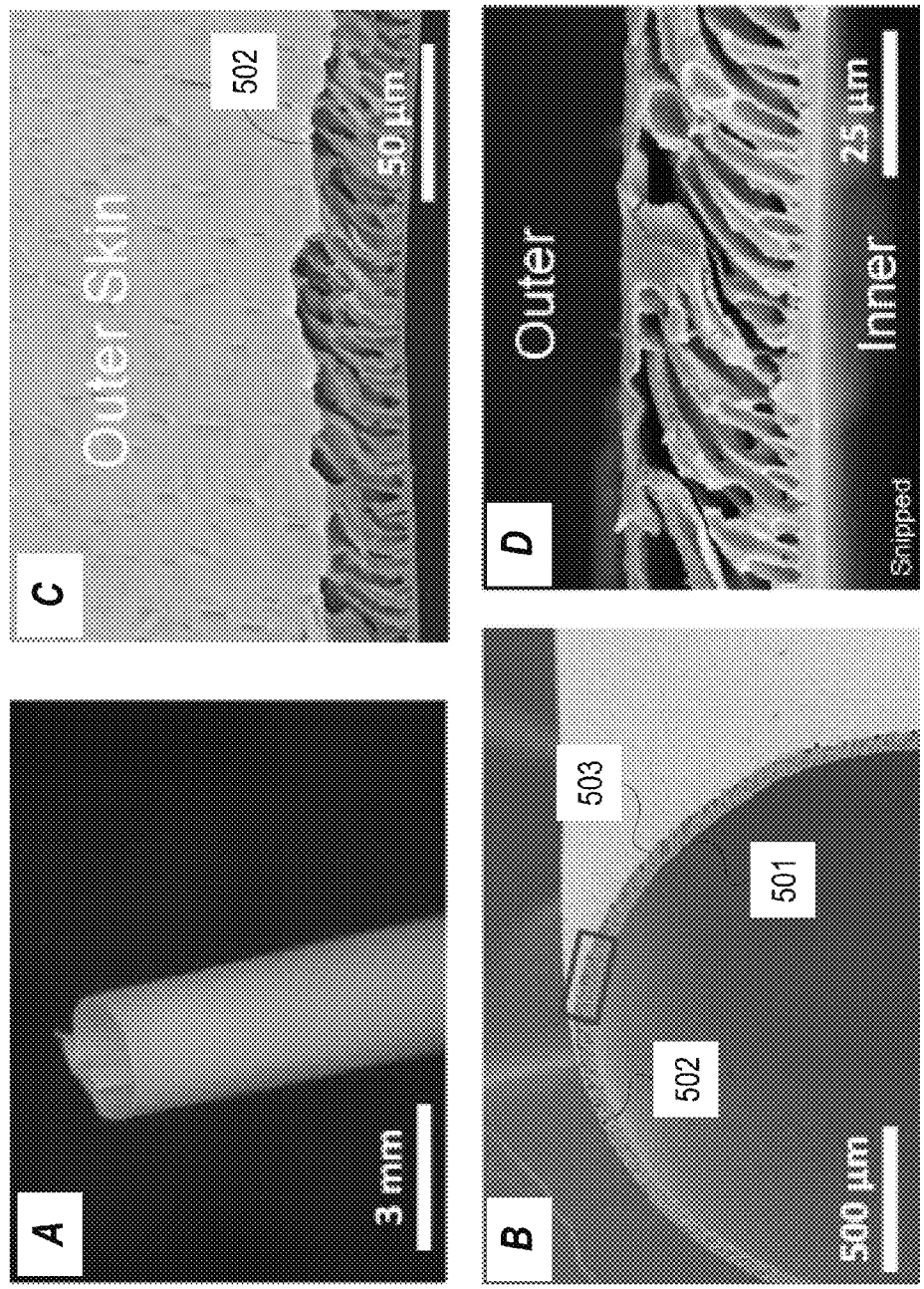
FIG. 5 illustrates micrographs of an example seeping flow catheter at various magnifications.

FIG. 5 shows micrographs of an example seeping catheter at various magnifications. Panel A of FIG. 5 illustrates a zoomed out view of the catheter. As described below in relation to FIG. 7, in some implementations, the seeping catheter is manufactured by rolling a sheet of porous material around a mandrel and the sealing the seam. Panel A of FIG. 5 illustrates the rolled porous material prior to the sealing of the seam to create the tube structure of the seeping catheter.

Panel B of FIG. 5 illustrates an end of the catheter illustrated in Panel A of FIG. 5. Panel B of FIG. 5 illustrates the inner face 501, the porous material 502, and the exterior face 503 of the catheter. Panel C of FIG. 5 is a micrograph of the boxed section in Panel B of FIG. 5 under higher magnification. Panel C of FIG. 5 illustrates the porous nature of the porous material 502. Panel C of FIG. 5 also illustrates that the exterior face 503 has been coated to create a lining that seals the porous material 502. Panel D of FIG. 5 is a micrograph illustrating a cutaway of the porous material 502. Panel D of FIG. 5 illustrates the pores that are created through the porous material 502, which enable fluid to flow substantially parallel to the central axis of the catheter.

FIGS. 6A-6D illustrate front and cross-sectional views of example multi-lumen flow catheters. In some implementations, the multi-lumen flow catheters do not include an inner porous material. As illustrated in FIGS. 6A-6D, and described in greater detail below, the multi-lumen catheter includes concentric walls defining a hollow space therebetween or a plurality of lumens running parallel (but not concentric) with one another. In some implementations, a fluid can be seeped (or flowed) through the inner face, outer face, catheter tip, or a combination thereof. In some implementations, the walls of the multiple lumens are substantially non-porous, and the fluid flows between the inner face, outer face, or a combination thereof through ports manufactured therein.

Figure 6A:
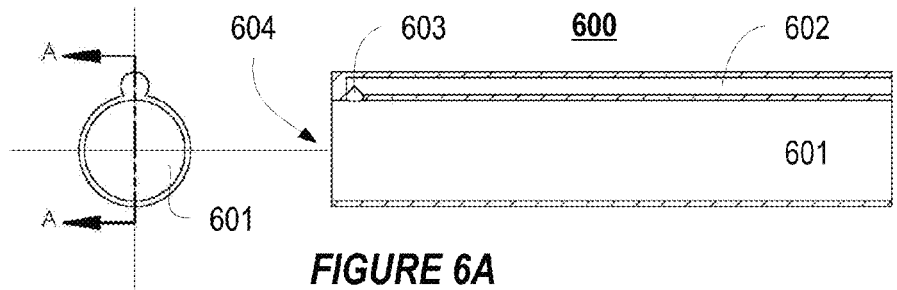
FIGS. 6A-6D illustrate front and cross-sectional views of example multi-lumen flow catheters.

FIG. 6A illustrates example front and cross-sectional views of an example multi-lumen flow catheter 600 with parallel lumens. Catheter 600 includes a primary lumen 601 and a secondary lumen 602. The primary lumen 601 and the secondary lumen 602 run parallel to one another and are non-concentric. The primary lumen 601 and the secondary lumen 602 are in fluidic communication with one another through a port 604. As illustrated in FIG. 6A, the port 604 is disposed toward the distal (or exit) tip 604 of the catheter 600. In some implementations, the tip 604 of the catheter 600 can be flushed by flowing a fluid through the secondary lumen 602. The fluid can be used to dislodge, flush, or clear material that can accumulate at or toward the tip 604 of the catheter 600. Having one or more ports 603 disposed toward the tip 604 of the catheter 600 enables the tip 604 to be flushed via the secondary lumen 602 with an inexpensive flushing agent (e.g., saline) rather than using the fluid within the primary lumen 601, which may be a costly therapeutic fluid.

Figure 6B:
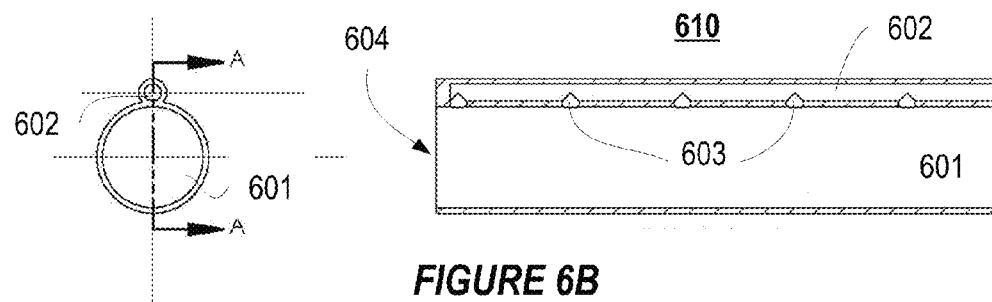

FIG. 6B illustrates example front and cross-sectional views of an example multi-lumen flow catheter 610 with parallel lumens. The catheter 610 includes a primary lumen 601 and a secondary lumen 602. The primary lumen 601 and the secondary lumen 602 run parallel to one another and are non-concentric. The primary lumen 601 and the secondary lumen 602 are in fluidic communication with one another through a plurality of ports 604 that run along the at least a portion of a length of the catheter 610. For example, the plurality of ports 604 may be disposed along only about the last 1% to about the last 20% of the catheter 610 or along substantially all of the catheter 610.

Figure 6C:
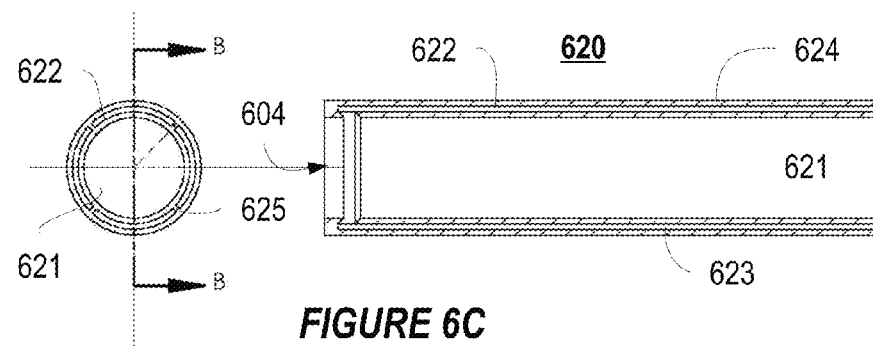

FIG. 6C illustrates example front and cross-sectional views of an example multi-lumen flow catheter 620 with multiple lumens defined by concentric walls. The catheter 620 includes a primary lumen 621 and a secondary lumen 622. The secondary lumen 622 is defined as the hollow space between an inner wall 623 and an outer wall 624. The hollow space (e.g., the secondary lumen 622) is maintained by one or more ribs 625 (also referred to as struts 625) that maintain the separation between the inner wall 623 and the outer wall 624. Each of the ribs 625 have a height between about 20 µm and about 2 mm, between about 20 µm and about 1 mm, or between about 20 µm and about 50 µm thick. The inner wall 623 terminates slightly prior to the tip 604 of the catheter 620. When the inner wall 623 terminates, fluid within the secondary lumen 622 enters the primary lumen 621. In some implementations, the inner wall 623 terminates at the tip 604 of the catheter 620, which causes the fluid within the secondary lumen 622 to exit at the tip of the catheter 620. In some implementations, the configuration illustrated in FIG. 6C is used to flush the tip of the catheter 620. In other implementations, the configuration is used to enable mixing of the fluids within the primary lumen 621 and the secondary lumen 622 substantially only toward the tip 604 of the catheter 620. As illustrated, catheter 620 includes four ribs distributed evenly about the circumference of the catheter 620. In some implementations, each of the ribs 625 run substantially the entire length of the catheter 620. In other implementations, each of the ribs 625 runs only a portion of the length of the catheter 620 and the catheter 620 includes a plurality of ribs 625 distributed about the circumference of the catheter 620 at a plurality of locations along the length of the catheter 620.

Figure 6D:
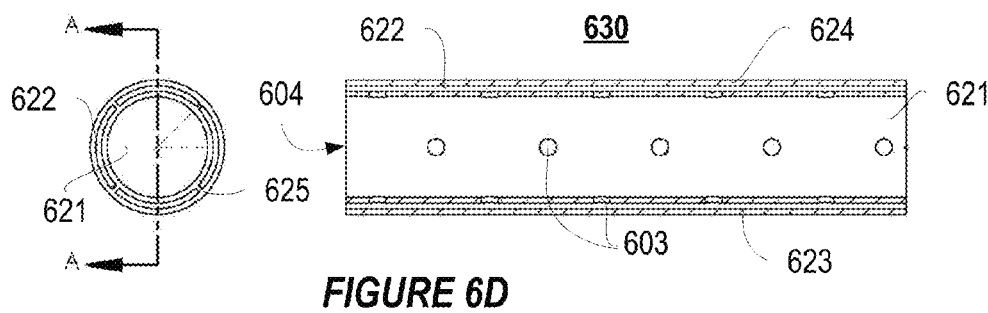

FIG. 6D illustrates an example front and cross-sectional view of an example multi-lumen flow catheter 630 with multiple lumens defined by concentric walls. The catheter 630 includes a primary lumen 621 and a secondary lumen 622. The spacing between an inner wall 623 and an outer wall 624 defines the secondary lumen 622. The spacing between the inner wall 623 and the outer wall 624 is maintained by a plurality of ribs 625. Fluidic communication is provided between the primary lumen 621 and the secondary lumen 622 via a plurality of ports 603 that run along a length of the catheter 630. In some implementations, the catheter 630 can include a plurality of ports 603 distributed across the outer face 624. The ports 603 distributed across the outer face 624 of the catheter 630 can be in addition to or in place of the ports 603 distributed across the inner face 623. In some implementations, a fluid flowing through the secondary lumen 622 exits through each of the ports 603 and creates a fluidic barrier that reduces the resistance to flow of a primary fluid through the primary lumen 621 by altering the boundary conditions, effectively increasing the internal diameter of the primary lumen 621. In some implementations, a fluid flowing through ports 603 distributed across the outer wall 624 can reduce encapsulation of the catheter 630. In some implementations, a fluid within the secondary lumen 622 exits substantially only through the plurality of ports 603 and in other implementations the fluid can also exit through the tip 604 of the catheter 630. In any of the above described multi-lumen flow catheters, one or more of the inner wall or outer walls can be a permeable membrane through which a fluid flowing through the secondary lumen can seep into the primary lumen and/or out of the catheter. In any of the multi-lumen flow catheters described herein, the walls of the catheter can include a thermoplastic, such as polystyrene, polycarbonate, polymethylmethacrylate, polyethersulfone, polysulfone, cyclic olefin copolymer, polyethylene; a cross-linked polymer, such as polydimethylsiloxane (PDMS), polyurethane, polyimide; a polymer material, such as polystyrene, cellulose acetate (CA), CN, polysulfone (PS), polyether sulfone (PES), polyacrilonitrile (PAN), polyamide, polyimide, polyetherimide (PEI), polyvinylidene fluoride (PVDF), polyvinylchloride (PVC), high-molecular-weight polyethylene, Teflon, poly(vinyl pyrrolidone) (PVP), polyethyleneglycol (PEG), tetronic 1307; a combination thereof; or any of the materials typically used to produce catheters.

Figure 7:
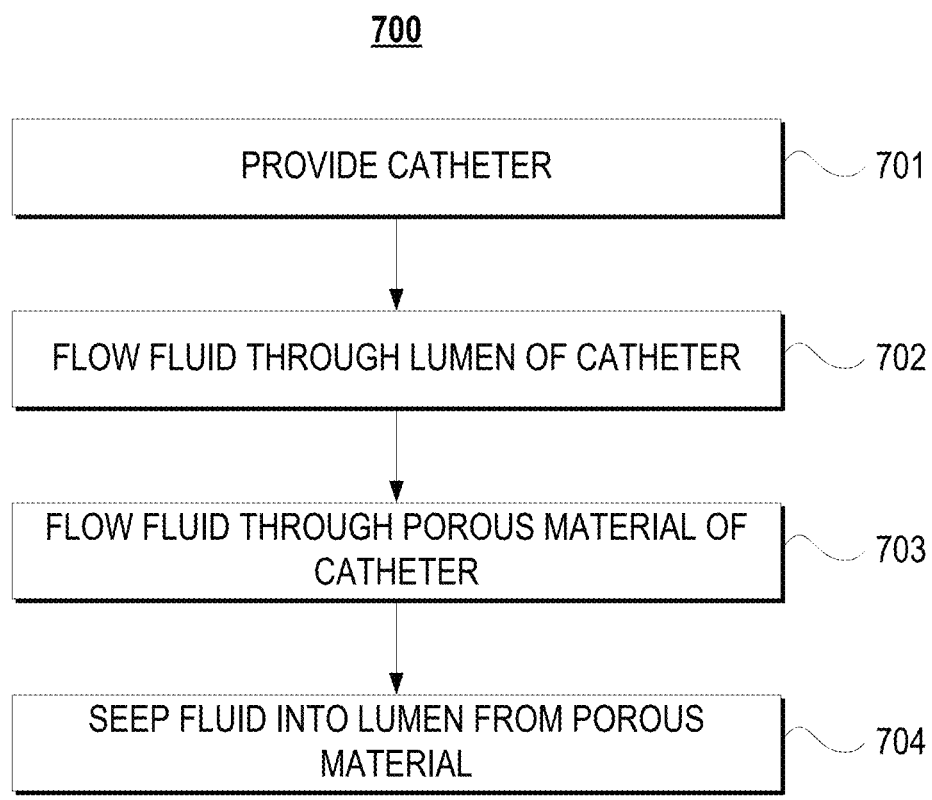
FIG. 7 is a flow chart of an example method for seeping fluid into a lumen of a catheter.

FIG. 7 illustrates a flow chart of an example method 700 for seeping fluid into a lumen of a catheter. The method 700 includes providing a seeping catheter (step 701). The method 700 also includes flowing fluid through the lumen of the catheter (step 702) and flowing fluid through the porous material of the catheter (703). As fluid flows through the porous material, the fluid seeps into the lumen of the porous material (step 704).

As set forth above and referring to FIG. 1, the method 700 begins with the provision of a seeping catheter (step 701). As described above, the catheter 101 includes a porous material 105. The inner face 104 of the porous material 105 defines the lumen 103 of the catheter 101. The porous material 105 also includes an exterior face 106.

In some implementations, the catheter is manufactured by rolling a sheet of porous material around a mandrel and then sealing the seam. In some implementations, the porous material includes a polymer material, such as polystyrene, cellulose acetate (CA), CN, polysulfone (PS), polyether sulfone(PES), polyacrilonitrile (PAN), polyamide, polyimide, polyetherimide (PEI), polyvinylidene fluoride (PVDF), polyvinylchloride (PVC), high-molecular-weight polyethylene, Teflon, or similar materials that create membranes through the phase inversion process. In some implementations, the porous material includes a blend of polymers. For example, PES can be blended with poly(vinyl pyrrolidone) (PVP) or polyethylenglycol (PEG). The porous material can also include surface treatments on linings such as tetronic 1307 and high-molecular-weight PEI. In some implementations, the porous material is manufactured by phase inversion of the polymer material. For example, the porous material sheet may be manufactured by mixing the polymer material with a solvent. The polymer solution is then cast into the desired shape. The casting is then submerged in a bath of nonsolvent, which displaces the solvent within the polymer casting. The release of the solvent from the polymer leaves a porous material. In some implementations, the solvent includes supercritical carbon dioxide, N-methyl-2-pyrrolidone (NMP), Dimethyl sulphoxide (DMSO) methylene chloride/1,1,2-trichloroethane, 2-methyl-2-butanol, dimethyl formamide, N,N-dimethylacetamide (DMAc), N,N-dimethylformamide (DMF), and triethyl phosphate (TEP).

In some implementations, the temperature of the bath, composition of the bath, the length of time the polymer casting is left in the bath, the initial thickness of the polymer casting, the initial surface characteristics of the polymer casting, the speed at which the polymer casting is extruded into and/or removed from the bath, and the ratio of the polymer to the solvent effect the porosity of the porous material. In some implementations, the porosity of the porous material is configured to limit, by molecular weight, the chemicals that can perfuse through the porous material or its faces. In some implementations, the porous material is a commercially available permeable membrane, or created using similar materials and processes as commercially available permeable membranes. Example commercially available permeable membranes can include those by TangenX (Novasep), Pall, Millipore, Fresenius, Gambro, Asahi Kasei-Kuraray, Kawasumi, Nikkiso, JMS Co., Nipro, Toray, Membrana. In other implementations, the porous material is created through an extrusion process.

In some implementations, one or more portions of the inner face and outer face are lined to substantially reduce the permeability of the lined portions. In some implementations, a lined face of the porous material is about 10, about 100, about 1000, or about 10000 times less permeable when compared to an unlined face or the permeability along an axis parallel to the central axis of the catheter. In some implementations, substantially no flow occurs through a lined face of the porous material when compared to the flow through an unlined face or the flow along an axis parallel to the central axis of the catheter. In some implementations, an unlined face is about 10, about 100, about 1000, or about 10000 times less permeable when compared to the permeability along an axis parallel to the central axis of the catheter. In some implementations, the unlined portions of the porous material have a flux between about 0.1 ml/(min*mmHg*m^2) and about 100 ml/(min*mmHg*m^2), between about 0.1 ml/(min*mmHg*m^2) and about 5 ml/(min*mmHg*m^2), between about 5 ml/(min*mmHg*m^2) and about 75 ml/(min*mmHg*m^2), between about 10 ml/(min*mmHg*m^2) and about 50 ml/(min*mmHg*m^2), or about 25 ml/(min*mmHg*m^2) and about 50 ml/(min*mmHg*m^2). In some implementations, the lining is created by coating the face with an adhesive, chemical vapor deposition, or exposing the face to a solvent or heat. The lining seals the pores and substantially prevents fluid from seeping through the treated surface.

As described above, the seeping catheter is manufactured by rolling a sheet of porous material around a mandrel and then sealing the seam. In some implementations, the lining is applied to the sheet of porous material prior to the porous material being rolled around a mandrel. In some implementations, a mask is applied to the sheet of porous material such that the lining is only applied to desired regions of the porous sheet. For example, to create a seeping catheter that is not lined toward its exiting tip, a mask may be applied toward one end of a sheet of porous material that will become the exiting tip. The sheet of porous material is then coated with an adhesive to form the lining. Once the adhesive has dried, the mask is removed. The adhesive was not able to reach the section of the sheet of porous material below the mask and thus that section of the porous sheet remains unlined. The sheet of porous material is then rolled to create a seeping catheter. In some implementations, a plurality of masks are used to create a plurality of linings along the inner and/or outer face of the porous material. In some implementations, the seeping catheter is manufactured by directly extruding the polymer casting in a hollow circle cross section shape directly into the phase inversion bath. In other implementations, the catheter is manufactured using a dry-wet spinning technique based on liquid-liquid phase separation. The method of manufacturing the catheter is selected responsive to the composition of the materials used to form the catheter in some implementations.

Referring again to FIG. 7, the method 700 includes flowing fluid through the lumen of the catheter (step 702) and flowing fluid through the porous material of the catheter (step 703). The fluid is injected into the porous material and the lumen of the catheter by a nozzle. As described in relation to FIG. 1, the nozzle 107 includes a secondary fitting 108 that is configured to inject the fluid into the porous material and a primary fitting 109 that is configured to inject the fluid into the lumen of the catheter. In some implementations, different fluids are injected into the porous material and into the lumen of the catheter. For example, blood may be flowed through the lumen of the catheter and a saline solution containing a blood thinner are flowed through the porous material 105 of the catheter.

The method also include seeping fluid into the lumen (step 704). As the fluid flows through the porous material of the catheter, the fluid seeps into the lumen of the catheter through the inner face of the catheter. In some implementations, the fluid also, or alternatively, seeps out of the catheter through the outer face of the catheter. As described in relation to FIG. 4, in some implementations, the inner face and outer face can be configured differently along the length of the catheter. For example, at one point in the catheter the inner face and the outer face of the catheter are lined such that fluid cannot seep out of the porous material, but at a second location along the length of the catheter the inner face may not be lined such that fluid can seep into the lumen of the catheter.

The invention may be embodied in other specific forms without departing from the spirit or essential characteristics thereof. The forgoing implementations are therefore to be considered in all respects illustrative, rather than limiting of the invention.

What is claimed:

1. A catheter comprising: an elongated tube having a distal end and a proximal end, the elongated tube comprising a porous material having an interior face and an exterior face, the interior face defining a lumen along a central axis of the elongated tube, the porous material being configured to flow a fluid substantially parallel to the central axis between the interior face and the exterior face of the porous material and to seep the fluid out of the porous material through the exterior face and interior face, a first section including a first outer lining covering the exterior face of the first section and configured to substantially limit perfusion of fluid through the exterior face of the first section, and an unlined section extending from a distal end of the first section, the interior and exterior faces of the unlined section including unlined porous material; and a fitting coupled to the proximal end of the elongated tube, the fitting configured to flow a first fluid into the porous material and a second fluid into the lumen.

2. The catheter of claim 1, wherein the first fluid is different than the second fluid.

3. The catheter of claim 1, wherein the resistance to flow through the inner face or exterior face of the porous material is between about 10 and about 100 times higher than the resistance to flow through the porous material along an axis parallel to the central axis of the elongated tube.

4. The catheter of claim 1, wherein the thickness of the porous material is between about 20 μm and about 1 mm.

5. The catheter of claim 1, wherein the porous material comprises phase inversion polyethersulfone.

6. The catheter of claim 1, where in the interior face has a first porosity at a first distance from the proximal end of the elongated tube and a second porosity at a second distance from the proximal end of the elongated tube.

7. The catheter of claim 1, wherein the elongated tube further comprises: a second section extending from a distal end of the unlined section and including a second outer lining covering the exterior face of the second section, the second outer lining configured to substantially limit perfusion of fluid through the exterior face of the second section; and an unlined tip portion extending from a distal end of the second section, the interior and exterior faces of the unlined tip section including unlined porous material.

8. The catheter of claim 7, wherein the second outer lining has a porosity greater than the first outer lining.

9. The catheter of claim 7, wherein the unlined tip portion of the elongated tube includes an open distal end providing for fluid flow out from the lumen of the elongated tube in a direction parallel to the central axis and for fluid to flow out from the porous material in a direction parallel to the central axis.

10. The catheter of claim 7, wherein the interior face of the second section of the elongated tube includes unlined porous material.

11. The catheter of claim 1, further comprising an inner lining covering the interior face of the first section of the elongated tube and configured to substantially limit perfusion of fluid through the interior face of the first section of the elongated tube.

12. The catheter of claim 11, wherein one or more of the first outer lining, the second outer lining, and the inner lining includes an adhesive coating.

13. The catheter of claim 11, wherein one or more of the first outer lining, the second outer lining, and the inner lining includes a surface of the porous material that has been melted to seal the pores of the surface of the porous material.

14. A catheter comprising: an elongated tube having a distal end and a proximal end, the elongated tube comprising a porous material having an interior face and an exterior face, the interior face defining a lumen along a central axis of the elongated tube, the porous material being configured to flow a fluid substantially parallel to the central axis between the interior face and the exterior face of the porous material and to seep the fluid out of the porous material through the exterior face and interior face; and a fitting coupled to the proximal end of the elongated tube, the fitting configured to flow a first fluid into the porous material and a second fluid into the lumen, the fitting including a collar disposed about a circumference of the catheter and configured to inject the first fluid into the porous material through the exterior face of the porous material.

* * * * *